US00PP37551P2

(12) United States Plant Patent
Nelson et al.

(10) Patent No.: US PP37,551 P2
(45) Date of Patent: Aug. 4, 2026

(54) STRAWBERRY PLANT NAMED 'S4A-448'

(50) Latin Name: *Fragaria ananassa*
Varietal Denomination: S4A-448

(71) Applicant: PLANT SCIENCES GENETICS, INC., Watsonville, CA (US)

(72) Inventors: Michael D. Nelson, Watsonville, CA (US); Samuel Estrada Trujillo, Watsonville, CA (US); Craig Mitchell Richael, Meridian, ID (US); Michele Lorraine Krucker, Boise, ID (US); Vanessa Nichole Roullier, Kuna, ID (US)

(73) Assignee: Plant Sciences Genetics, Inc., Watsonville, CA (US)

( * ) Notice: Subject to any disclaimer, the term of this patent is extended or adjusted under 35 U.S.C. 154(b) by 0 days.

(21) Appl. No.: 19/279,959

(22) Filed: Jul. 24, 2025

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./208, 209
See application file for complete search history.

(56) References Cited

U.S. PATENT DOCUMENTS

PP29,794 P2 11/2018 Nelson et al.
PP35,703 P3 3/2024 Blaker

*Primary Examiner* — Susan McCormick Ewoldt
(74) *Attorney, Agent, or Firm* — FOLEY & LARDNER LLP

(57) ABSTRACT

This invention relates to a new and distinct variety of strawberry plant named 'S4A-448'. This new strawberry plant named 'S4A-448' is primarily adapted to the growing conditions of West Central Florida, and is primarily characterized by its orange red fruit color, medium berry size, high marketable yield, medium to strong plant vigor, and medium plant density.

7 Drawing Sheets

Latin name of the genus and species of the plant claimed: *Fragaria ananassa.*

Variety denomination: 'S4A-448'.

BACKGROUND OF THE INVENTION

The present invention relates to a new and distinct strawberry plant variety named 'S4A-448'. This new variety is a result of using CRISPR-Cas9 to target a gene which controls flowering habit in the 'Inspire' variety (U.S. Plant Pat. No. 29,794), to suppress its function and alter the plant phenotype, resulting in increased flowering and fruit yield. The target gene is a floral repressor, and its expression is altered by photo period and temperature. As temperature and day-length increases, expression of the gene also increases, and flower production is reduced. The knockout of three or more alleles of the target gene in short-day strawberry varieties can result in a spectrum of flowering changes, including earlier flowering, increased flowering, insensitivity to day-length in flowering response (day-neutrality), and/or increased fruit yield. In the case of the genetically edited strawberry variety 'S4A-448', the knockout of alleles in the gene resulted in earlier flowering, increased flowering and fruiting across the entire fruit harvest season, and day-neutral flowering, compared to the non-edited original variety 'Inspire' (U.S. Plant Pat. No. 29,794). The variety is botanically known as *Fragaria ananassa.*

The genetic edit was made in Boise, Idaho in 2020 and was selected from a control trial plot in Hillsborough County, Florida. After its selection, the new variety was asexually propagated by stolons in both Siskiyou County, California and San Joaquin County, California. The new variety was extensively tested over the next several years in fruit production fields in Hillsborough County, Florida. This propagation has demonstrated that the combination of some phenotypic traits along with genotypic data (as disclosed herein) as characterizing the novel variety are fixed and remain true-to-type through successive generations of asexual reproduction.

BRIEF SUMMARY OF THE INVENTION

'S4A-448' is primarily adapted to the climate and growing conditions of West Central Florida. The subtropical climate of West Central Florida provides the day length and moderate temperatures needed to produce an early yielding, vigorous plant and maintain fruit quality during the fall and winter production months.

The following traits have been repeatedly observed and are determined to be unique characteristics of 'S4A-448', which in combination distinguish this strawberry plant as a new and distinct variety:

1. Orange red fruit color;
2. Medium berry size;
3. High marketable yield;
4. Medium to Strong plant vigor; and
5. Medium plant density.

The strawberry variety 'Inspire' (U.S. Plant Pat. No. 29,794) was used as the comparison standard. Much of the phenotypic data is similar to Inspire and but some consequential differences were observed. In side-by-side comparisons from the 2024-2025 season (Dec. 5, 2024 to Mar. 15, 2025), 'S4A-448' compares with 'Inspire' (U.S. Plant Pat. No. 29,794) in the following combination of characteristics as described in Table 1.

TABLE 1

| Characteristic | 'S4A-448' | 'Inspire' (U.S. Plant Pat. No. 29,794) |
|---|---|---|
| Plant: vigor | Ranges from medium to strong | Very Strong |
| Plant: density (1-5:dense-open) | 3 | 2 |
| Season marketable yield (gm/plt) | 320 | 140 |
| Fruit: Season average berry size (gm) | 19.8 | 21.0 |

Strawberry variety 'SB_14_028-025' (U.S. Plant Pat. No. 35,703) was used as another comparison to 'S4A-448'. In side-by-side comparison 'SB_14_028-025' (U.S. Plant Pat. No. 35,703) and 'S4A-448' differ by the following combination of characteristics as described in Table 2.

TABLE 2

| Characteristic | 'S4A-448' | 'SB_14_028-025' (U.S. Plant Pat. No. 35,703) |
|---|---|---|
| Plant: vigor | Ranges from medium to strong | Low |
| Fruit: size | Medium | Very large |
| Fruit: Season average berry size (gm) | 19.8 | 34.1 |
| Fruit: Hollow center expression | Weak | Moderate |

BRIEF DESCRIPTIONS OF THE PHOTOGRAPHS

The accompanying color photographs illustrate the overall appearance of typical specimens of the new strawberry variety 'S4A-448' at various stages of development, as true as it is reasonably possible with color reproductions of this type. Color in the photographs may differ slightly from the color value cited in the botanical descriptions which accurately describe the color of 'S4A-448'. The depicted plant and plant parts of the new strawberry variety 'S4A-448' are approximately four months old. The photographs were taken in Hillsborough County, Florida.

Figure 1:
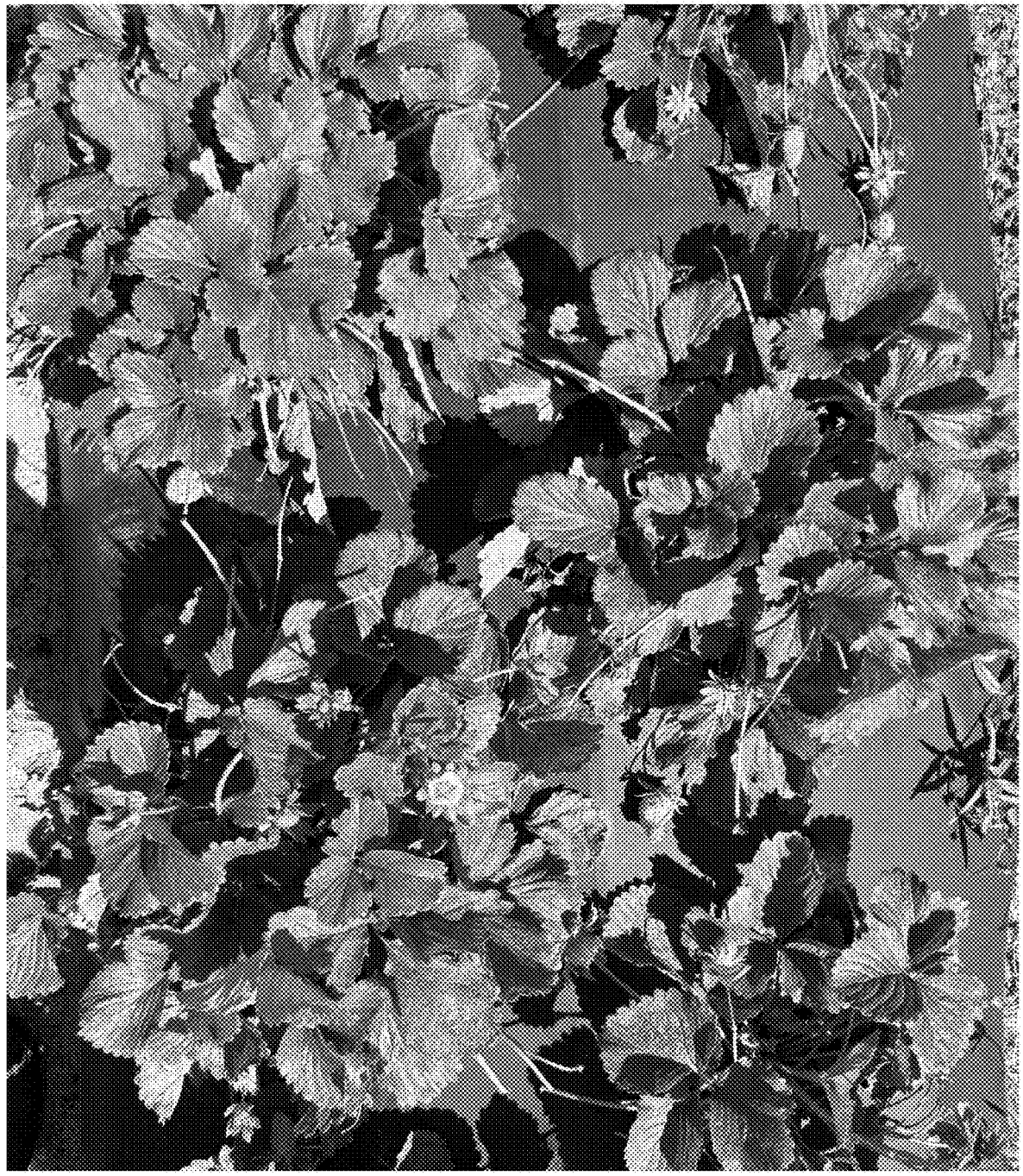
FIG. 1 shows typical fruiting field characteristics of 'S4A-448', taken in the month of March 2025.
Figure 2:
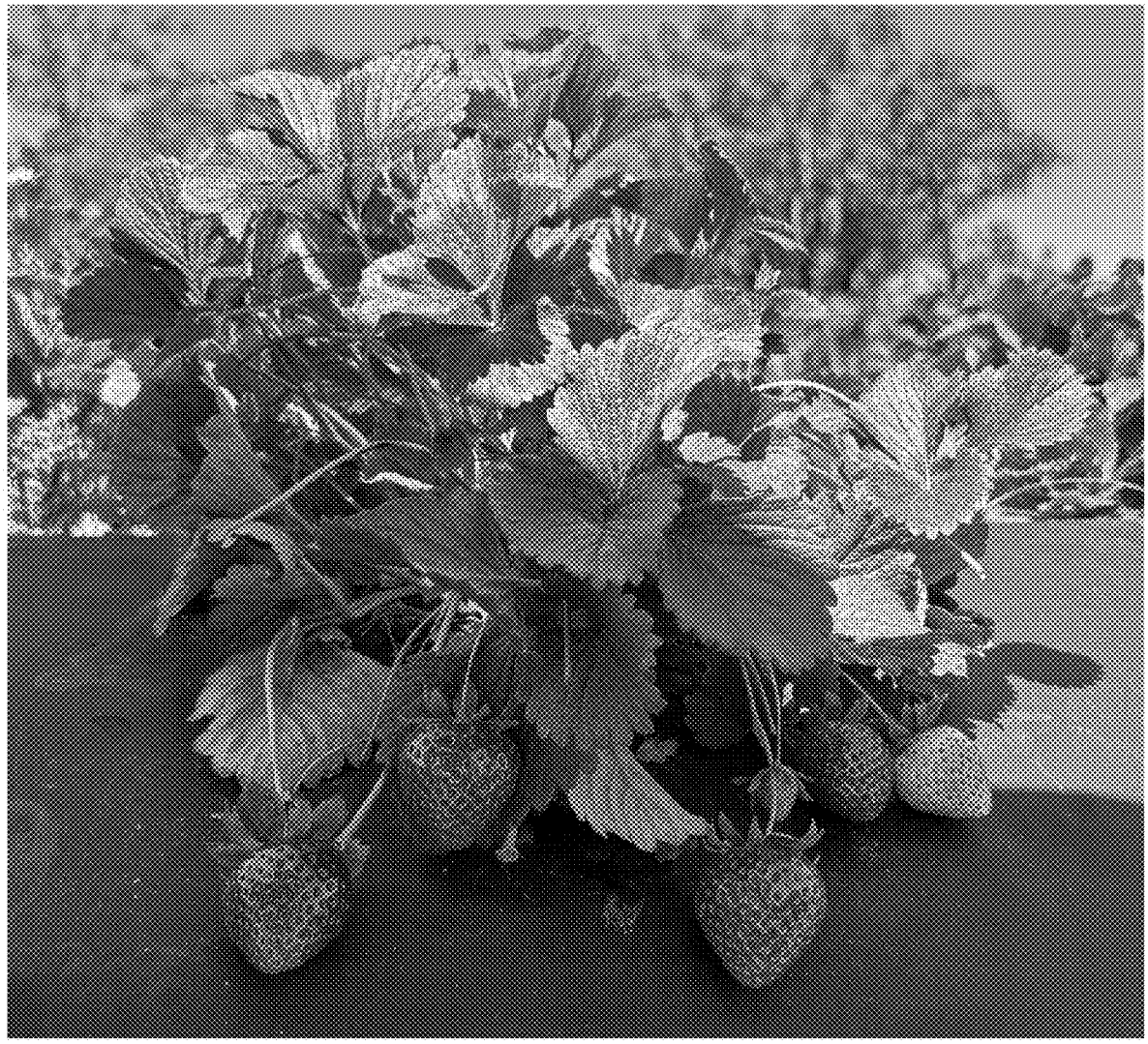
FIG. 2 shows a close-up view of a typical plant of 'S4A-448', taken in the month of March 2025.
Figure 3:
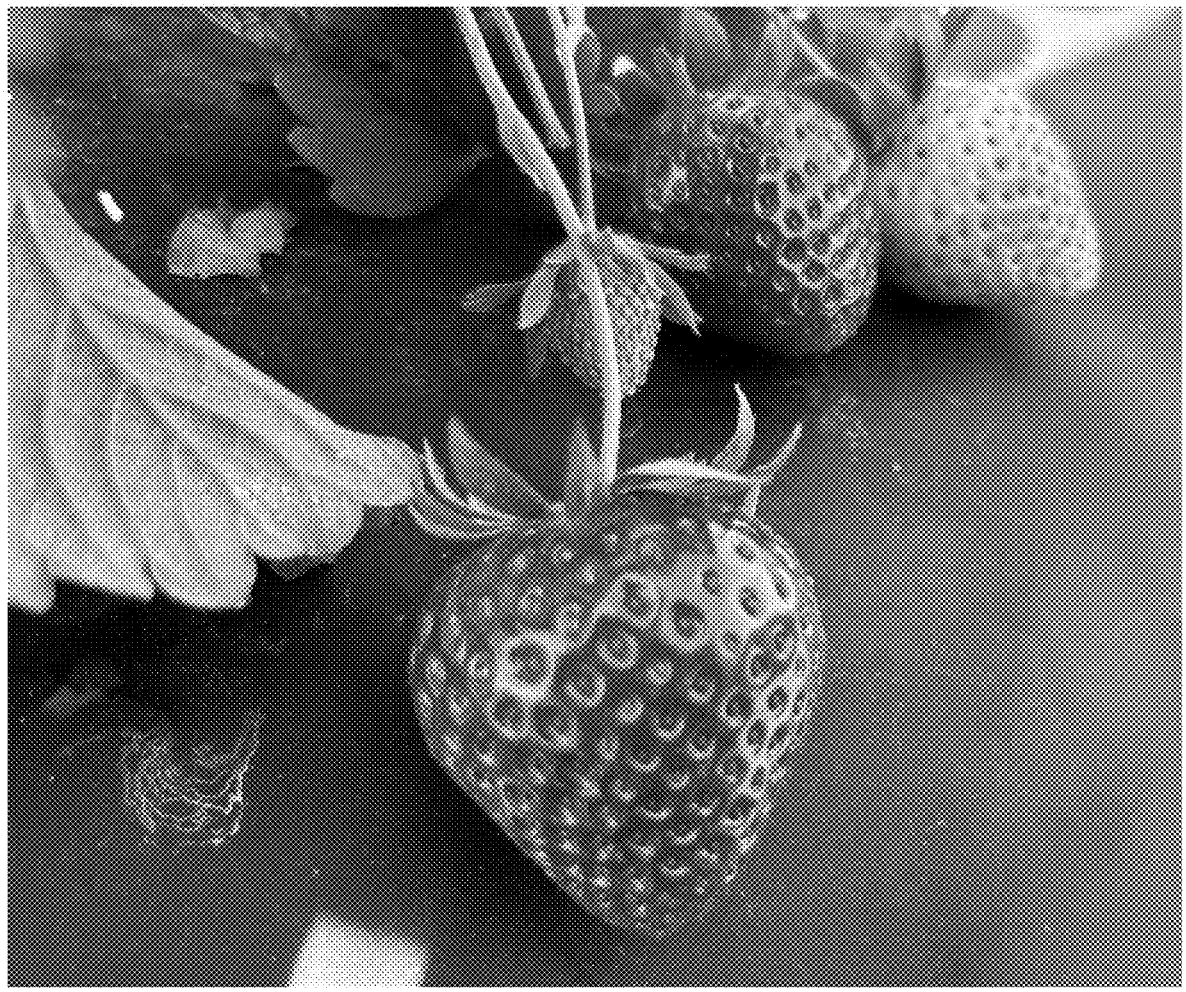
FIG. 3 shows typical mature and immature field fruit of 'S4A-448', taken in the month of March 2025.
Figure 4:
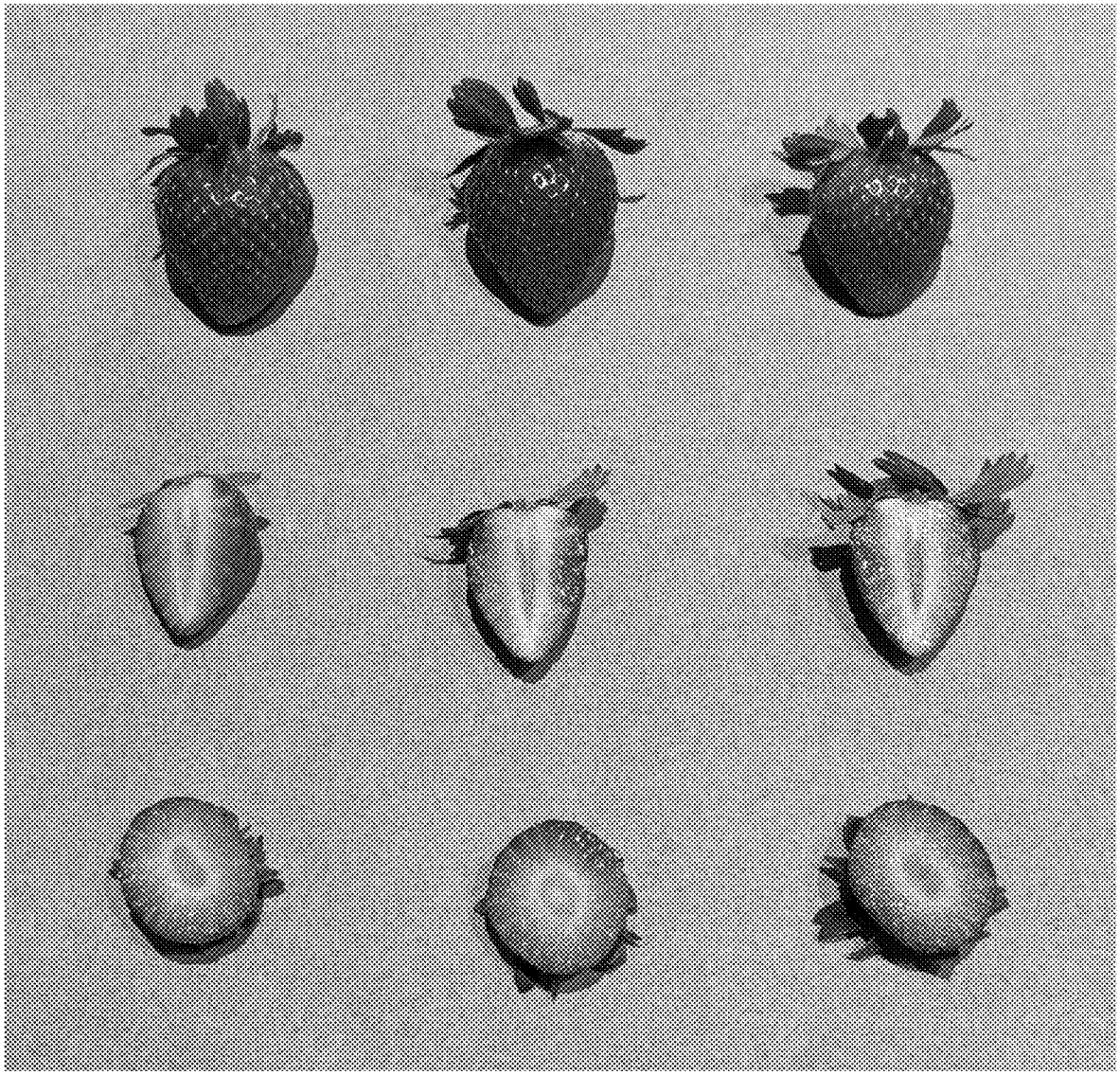
FIG. 4 shows typical internal and external mature fruit characteristics of 'S4A-448', taken in the month of March 2025.
Figure 5A:
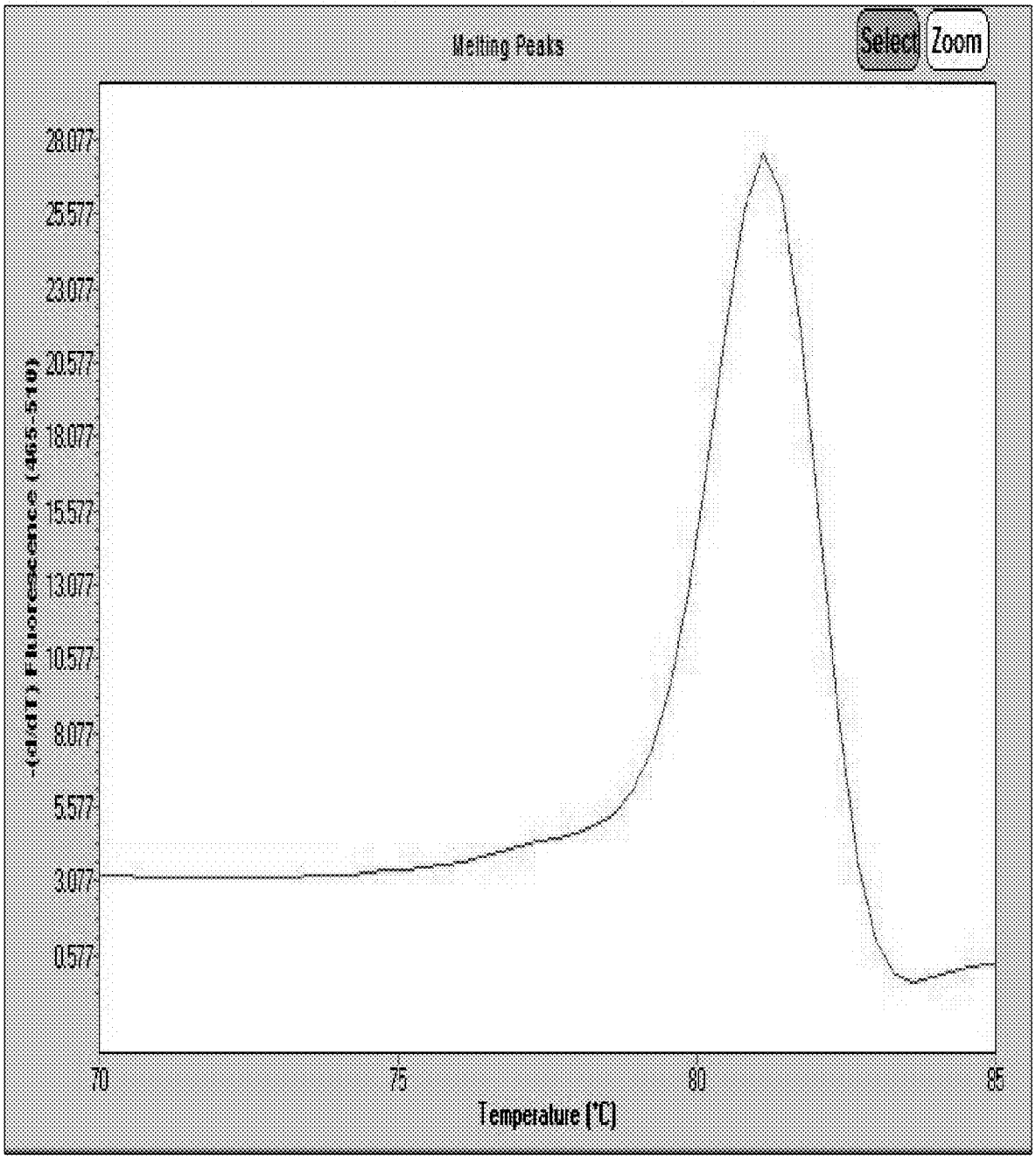
Figure 5B:
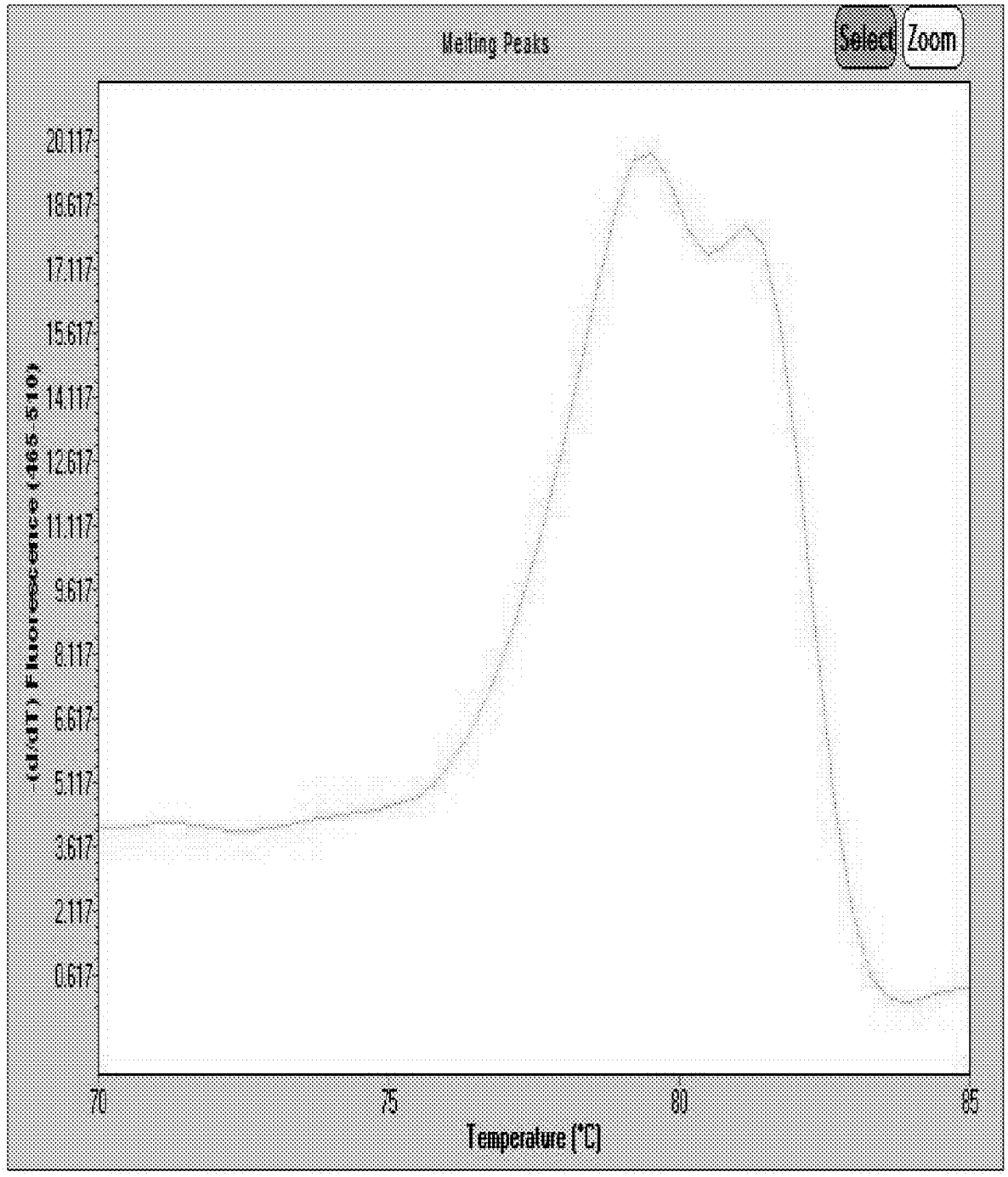
Figure 5C:
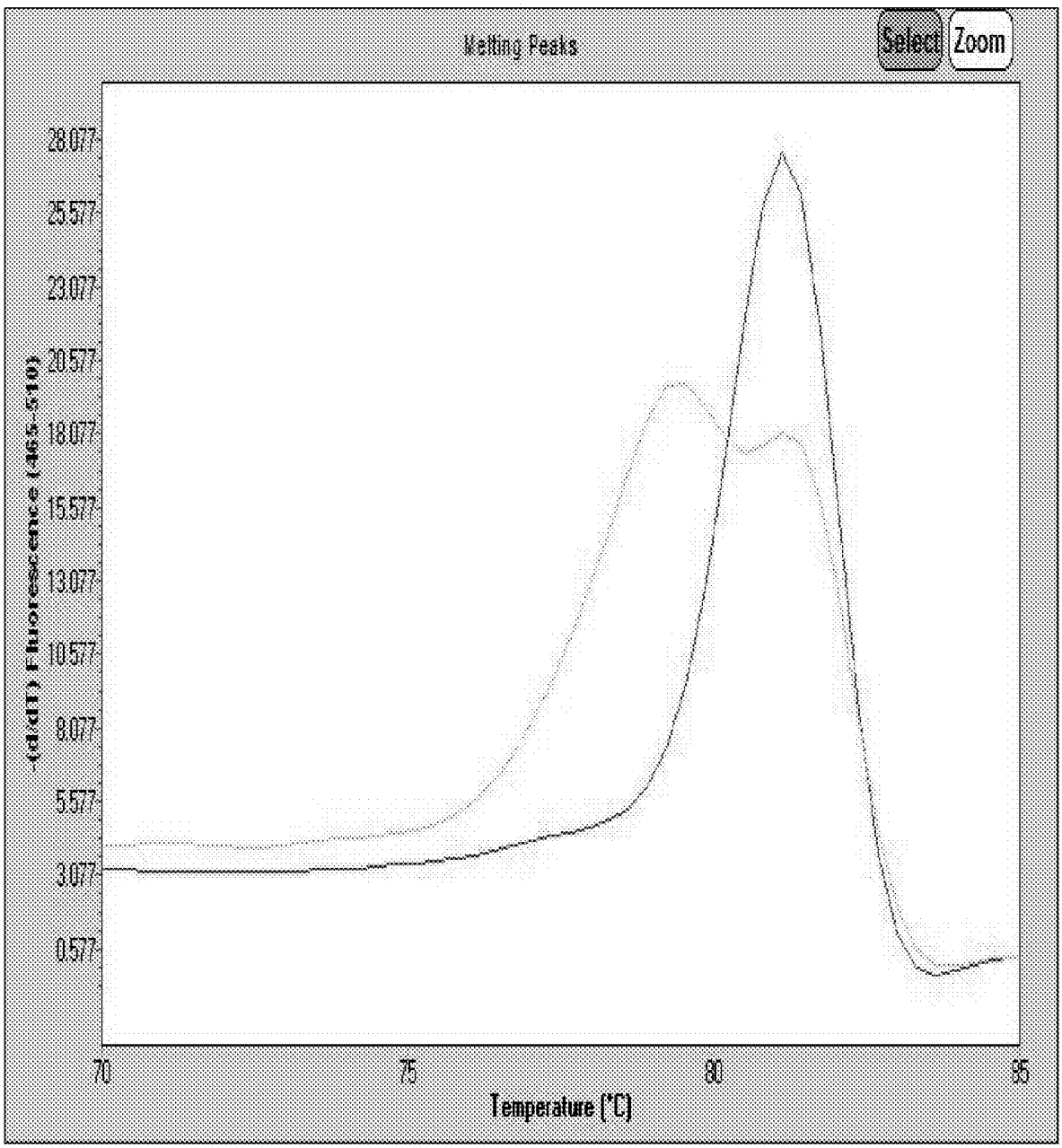

FIGS. 5A-5C show the significant difference between 'Inspire' and 'S4A-448' as described in Table 1. Primers for polymerase chain reaction (PCR) were created on either side of the edit, to amplify the sequence that was edited. FIG. 5A shows the shows the PCR high-resolution melting (HRM) curve result for 'Inspire'. FIG. 5B shows the PCR-HRM curve result for the edited 'S4A-448' line. FIG. 5C shows the PCR-HRM results of these two varieties compared to each other.

The results of this molecular DNA test clearly demonstrate that these two varieties are genotypically different from one another.

DETAILED BOTANICAL DESCRIPTION

The new variety 'S4A-448' has not been observed under all possible environmental conditions. The characteristics of the new variety 'S4A-448' may vary in detail, depending upon variations in environmental factors, including weather (temperature, humidity and light intensity), day length, soil type and location. In addition, the characteristics of any comparison variety included in Table 1 and of the present invention may vary in detail, depending upon variations in environmental factors, including weather (temperature, humidity and light intensity), day length, soil type and location.

The aforementioned photographs, together with the following phenotypic and genotypic description of the new variety 'S4A-448', unless otherwise noted, are based on observations taken during the 2024-2025 growing season in Hillsborough County, Florida. These measurements and ratings were taken from plants of 'S4A-448' dug from a high-elevation nursery located in Siskiyou County, California during late September 2024 and planted approximately one month later in Hillsborough County, Florida. The planting date was significantly delayed due to a series of hurricanes across Florida during the month of October 2024. The approximate age of the observed plants is four to five months. Yield observations including average weight and marketable yield, along with fruit quality characteristic, were measured during the 2024-2025 growing season. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London, Sixth Edition (2019 Reprint).

The following characteristics describe fruit, plant, stolon, foliage, fruiting truss, flower, reproductive organs and pest and disease characteristics of the new strawberry 'S4A-448'.

Fruit characteristics:

*Color of mature fruit*.—RHS N34B (orange red).

*Color of internal flesh* (*excluding core*).—RHS 34C (medium red).

*Color of core*.—RHS 39B (light red).

*Average length* (*cm*).—4.1.

*Average width* (*cm*).—3.5.

*Size*.—Medium.

*Average length/width ratio*.—1.2 (Slightly longer than broad).

*Hollow center expression*.—Weak.

*Season average weight* (*gm*).—19.8.

*Marketable yield season* (*gm/plant*).—320.

*Predominant shape*.—Conical.

*Difference in shape between primary and secondary fruit*.—None or very slight.

*Band without achenes*.—Narrow.

*Evenness of surface*.—Even or very slightly uneven.

*Evenness of color*.—Even or very slightly uneven.

*Glossiness*.—Strong.

*Insertion of achenes*.—Slightly above surface.
*Average calyx diameter* (*cm*).—5.0.
*Position of calyx attachment*.—Inserted.
*Attitude of sepals*.—Ranges from outward to upward.
*Size of calyx in relation to fruit diameter*.—Smaller.
*Adherence of calyx* (*when fully ripe*).—Strong.
*Firmness of flesh* (*gf*).—377.5 (Ranges from medium to firm).
*Keeping quality*.—Excellent.
*Fruit market*.—Fresh.
*Distribution of red color of the flesh*.—Marginal and central.
*Sweetness*.—Very good.
*Achene average length* (*mm*).—1.3.
*Achene average width* (*mm*).—0.9.
*Achene average weight* (*mg*).—0.6.
*Achene average quantity per berry*.—387.
*Achene shape*.—Elliptic.
*Time of first flowering*.—Early (mid to late-October in Hillsborough County, Florida).
*Flowering season*.—October-March.
*Time of first fruit*.—Early (late-November in Hillsborough County, Florida).
*Fruiting season*.—November-March.
*Post-harvest fruit longevity*.—10-14 days, if stored according to industry standards.
*Type of bearing*.—Remontant (day neutral).

Plant characteristics:
*Average height* (*cm*).—23.3.
*Average spread* (*cm*).—30.3.
*Size*.—Medium.
*Habit*.—Upright.
*Density*.—Medium.
*Vigor*.—Ranges from medium to strong.

Stolon characteristics:
*Color*.—RHS N146C (yellow green group).
*Anthocyanin coloration*.—RHS 181B (greyed red group).
*Anthocyanin intensity*.—Medium to weak.
*Pubescence*.—Medium.
*Attitude of hairs*.—Upward.
*Average quantity in nursery* (*per square foot*).—5 to 6 (medium).

Terminal leaf characteristics:
*Average length* (*cm*).—8.1.
*Average width* (*cm*).—6.7.
*Average area terminal* ($cm^2$).—53.9.
*Average length/width ratio*.—1.2 (longer than broad).
*Shape of base*.—Acute.
*Shape of apex*.—Obtuse.
*Margins* (*shape of teeth*).—Obtuse (serrate to crenate).
*Average serrations per leaf*.—18.8.

Foliage characteristics:
*Color of upper surface*.—RHS NN137B (medium green).
*Color of lower surface*.—RHS 137C (green group).
*Number of leaflets*.—3.
*Foliage size*.—Medium.
*Average length* (*cm*).—11.5.
*Average width* (*cm*).—13.5.
*Average area foliage* ($cm^2$).—154.7.
*Shape in cross section*.—Slightly concave.
*Interveinal blistering*.—Medium.
*Venation pattern*.—Pinnate.
*Leaf glossiness*.—Medium.
*Leaf variegation*.—Absent.

Petiole characteristics:
*Petiole color*.—RHS 144A (yellow green group).
*Average length* (*cm*).—13.5.
*Average diameter* (*mm*).—2.74.
*Average size*.—Medium.
*Attitude of hairs*.—Strongly outward.
*Frequency of bract leaflets*.—0% occurrence (none).
*Size of bract leaflets*.—N/A.
*Pubescence*.—Moderate.
*Petiolule color*.—RHS 144D (yellow green group).
*Petiolule average length* (*mm*).—14.7.
*Petiolule average diameter* (*mm*).—1.73.

Stipule characteristics:
*Color*.—RHS 144D (yellow green group).
*Anthocyanin coloration*.—RHS 56B (red group).
*Anthocyanin intensity*.—Absent or very weak.
*Average length* (*mm*).—32.7.
*Average width* (*mm*).—7.6.
*Shape*.—Triangular.
*Margin*.—Smooth.
*Texture*.—Smooth to Moderate.

Fruiting truss characteristics:
*Anthocyanin coloration*.—RHS 181C (greyed red group).
*Anthocyanin intensity*.—Absent or very weak.
*Average length at maturity* (*cm*).—18.11.
*Position relative to foliage*.—Ranges from level with to above.
*Flower quantity* (*season average per plant*).—48.
*Average fruit quantity per truss*.—5.2.
*Attitude at first pick*.—Prostrate.
*Primary pedicel color*.—RHS 144C (yellow green group).
*Primary pedicel average length* (*cm*).—6.4.
*Primary pedicel average diameter* (*mm*).—1.6.
*Pedicel attitude of hairs*.—Slightly outwards.
*Pedicel pubescence*.—Weak.
*Primary peduncle color*.—RHS 144C (yellow green group).
*Primary peduncle average length* (*cm*).—9.7.
*Primary peduncle average diameter* (*mm*).—2.5.
*Peduncle pubescence*.—Weak.

Flower characteristics:
*Petal color, upper surface*.—RHS NN155C (white group).
*Petal color, lower surface*.—RHS NN155C (white group).
*Petal average length* (*mm*).—14.0.
*Petal average width* (*mm*).—12.7.
*Petal average length/width ratio*.—1.1 (longer than broad).
*Average petal quantity per flower*.—5.9.
*Petal shape*.—Orbicular.
*Petal pubescence*.—Smooth.
*Petal shape of base*.—Obtuse.
*Petal shape of apex*.—Obtuse/rounded.
*Petal margins*.—Smooth.
*Sepal color, upper surface*.—RHS 137B (green group).
*Sepal color, lower surface*.—RHS 138B (green group).
*Sepal average length* (*mm*).—24.0.
*Sepal average width* (*mm*).—12.3.
*Sepal average length/width ratio*.—2.0.
*Average sepal quantity per flower*.—11.0.
*Sepal shape*.—Cuneate.

*Sepal pubescence*.—Light.
*Sepal shape of apex*.—Obtuse.
*Sepal margins*.—Entire.
*Flower bud color*.—RHS 144C (yellow green group).
*Flower bud shape*.—Pyriform.
*Flower bud average length* (*mm*).—25.2.
*Flower bud average diameter* (*mm*).—8.7.
*Corolla average diameter* (*mm*).—33.6 (large).
*Flower average depth* (*mm*).—10.8.
*Calyx average diameter* (*mm*).—53.2.
*Size of calyx relative to corolla*.—Larger.
*Arrangement of petals*.—Overlapping.
*Size of inner calyx relative to outer calyx*.—Same.

Reproductive organs:

*Anther color*.—RHS 12A (yellow group).
*Filament color*.—RHS 157C (green, white group).
*Stamen*.—Present.
*Filament average length* (*mm*).—3.1.
*Anther average length* (*mm*).—1.6.
*Anther shape*.—Ovoid.
*Pollen amount*.—Abundant.
*Pollen color*.—RHS 12A (yellow group).
*Ovary color*.—RHS 1D (green, yellow group).
*Style color*.—RHS 157C (green, white group).
*Pistil average quantity per flower*.—386.6.
*Pistil average length* (*mm*).—1.0.
*Style average length* (*mm*).—0.8.
*Stigma average diameter* (*mm*).—<0.1.
*Stigma shape*.—Simple.

Disease and pest reactions:

*Powdery mildew* (*Sphaerotheca macularis*).—Moderate resistant.
*Botrytis fruit rot* (*Botrytis cinerea*).—Moderately susceptible.
*Fusarium wilt* (*Fusarium oxysporum*).—Susceptible.
*Two-spotted spider mite* (*Tetranychus urticae*).—Moderately susceptible.

We claim:

1. A new and distinct strawberry plant named 'S4A-448', as herein described in the specification as set forth above.

* * * * *